US009009493B2

(12) United States Patent
Leighton

(10) Patent No.: US 9,009,493 B2
(45) Date of Patent: *Apr. 14, 2015

(54) METHOD AND SYSTEM FOR HANDLING SENSITIVE DATA IN A CONTENT DELIVERY NETWORK

(71) Applicant: Akamai Technologies, Inc., Cambridge, MA (US)

(72) Inventor: F. Thomson Leighton, Newtonville, MA (US)

(73) Assignee: Akamai Technologies, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/450,218

(22) Filed: Aug. 2, 2014

(65) Prior Publication Data

US 2014/0337238 A1 Nov. 13, 2014

Related U.S. Application Data

(63) Continuation of application No. 12/960,840, filed on Dec. 6, 2010, now Pat. No. 8,799,674.

(60) Provisional application No. 61/266,535, filed on Dec. 4, 2009.

(51) Int. Cl.
*H04L 29/06* (2006.01)
*G06F 21/60* (2013.01)
*H04W 12/00* (2009.01)
*G06Q 20/38* (2012.01)

(52) U.S. Cl.
CPC .......... *H04L 63/0428* (2013.01); *G06F 21/602* (2013.01); *H04W 12/00* (2013.01); *G06Q 20/3829* (2013.01); *G06Q 2220/00* (2013.01); *H04L 2463/102* (2013.01)

(58) Field of Classification Search
CPC ..... G06F 21/60; G06F 21/6245; G06F 21/602; H04L 63/0428
USPC ....................................... 713/189, 171; 726/6
See application file for complete search history.

(56) References Cited

U.S. PATENT DOCUMENTS

| 6,304,915 | B1* | 10/2001 | Nguyen et al. ................. 709/250 |
| 7,324,972 | B1* | 1/2008 | Oliver et al. ..................... 705/40 |
| 2006/0168088 | A1* | 7/2006 | Leighton et al. ............... 709/207 |
| 2008/0263645 | A1* | 10/2008 | Renter et al. ....................... 726/6 |

OTHER PUBLICATIONS

Liver, B.; Tice, K.; , "Privacy Application Infrastructure: Confidential Data Masking," Commerce and Enterprise Computing, 2009. CEC '09. IEEE Conference on , vol., No., pp. 324-332, Jul. 20-23, 2009.*
Jing-Jang Hwang, Tzu-Chang Yeh, Jung-Bin Li, Securing on-line credit card payments without disclosing privacy information, Computer Standards & Interfaces, vol. 25, Issue 2, May 2003, pp. 119-129, ISSN 0920-5489, 10.1016/S0920-5489(02)00102-2.*

* cited by examiner

*Primary Examiner* — Syed Zaidi
(74) *Attorney, Agent, or Firm* — David H. Judson

(57) ABSTRACT

Using cryptographic techniques, sensitive data is protected against disclosure in the event of a compromise of a content delivery network (CDN) edge infrastructure. These techniques obviate storage and/or transfer of such sensitive data, even with respect to payment transactions that are being authorized or otherwise enabled from CDN edge servers.

10 Claims, 2 Drawing Sheets

US 9,009,493 B2

METHOD AND SYSTEM FOR HANDLING SENSITIVE DATA IN A CONTENT DELIVERY NETWORK

TECHNICAL FIELD

This application relates generally to the protection of sensitive data, such as credit card information, in a networked environment.

BRIEF DESCRIPTION OF THE RELATED ART

Distributed computer systems are well-known in the prior art. One such distributed computer system is a "content delivery network" or "CDN" that is operated and managed by a service provider. The service provider typically provides the content delivery service on behalf of third parties. A "distributed system" of this type typically refers to a collection of autonomous computers linked by a network or networks, together with the software, systems, protocols and techniques designed to facilitate various services, such as content delivery or the support of outsourced site infrastructure. Typically, "content delivery" means the storage, caching, or transmission of content, streaming media and applications on behalf of content providers, including ancillary technologies used therewith including, without limitation, DNS query handling, provisioning, data monitoring and reporting, content targeting, personalization, and business intelligence.

The distributed and shared network infrastructure as described above is used, among other purposes, to deliver content from a plurality of web sites. Representative web sites include e-commerce retailers at which end users may shop and purchase products and services. In the prior art, CDN service providers provide the content delivery for these on-line retailers but, when it comes time for an end user to complete a purchase, the associated payment services typically are handled by third parties. In part, this is because such payment services involve the processing and storage of sensitive data, such as end user credit card data.

BRIEF SUMMARY

Using cryptographic techniques, sensitive data is protected against disclosure in the event of a compromise of a content delivery network (CDN) edge infrastructure. These techniques obviate storage and/or transfer of such sensitive data, even with respect to payment transactions that are being authorized or otherwise enabled from CDN edge servers.

The foregoing has outlined some of the more pertinent features of the disclosed subject matter. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION

Figure 1:
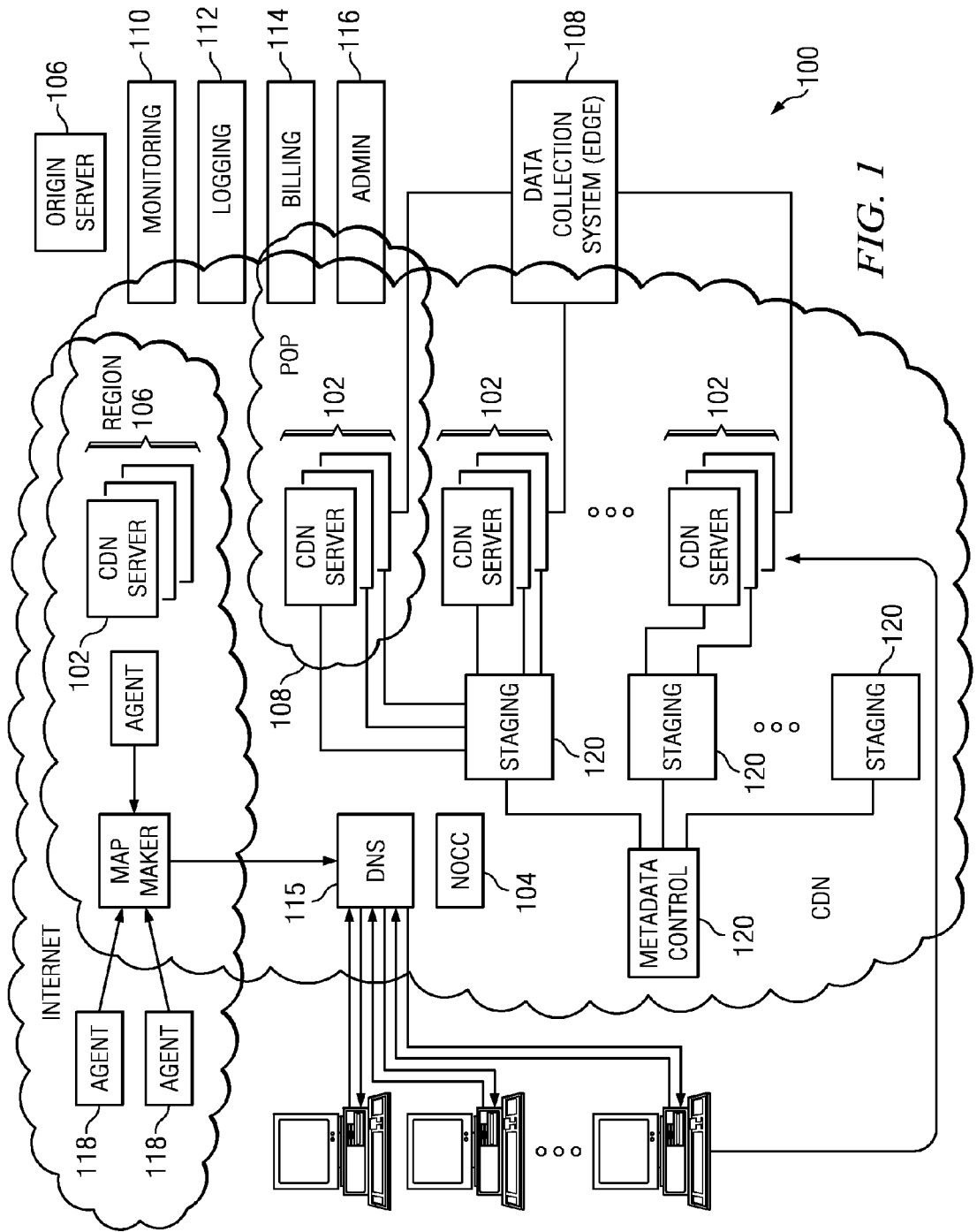
FIG. 1 is a simplified block diagram of a content delivery network (CDN) in which the disclosed techniques herein may be implemented.

In a known system, such as shown in FIG. 1, a distributed computer system 100 is configured as a content delivery network (CDN), and it is assumed to have a set of machines 102a-n distributed around the Internet. Typically, most of the machines are servers located near the edge of the Internet, i.e., at or adjacent end user access networks. A network operations command center (NOCC) 104 manages operations of the various machines in the system. Third party sites, such as web site 106, offload delivery of content (e.g., HTML, embedded page objects, streaming media, software downloads, and the like) to the distributed computer system 100 and, in particular, to "edge" servers. Typically, content providers offload their content delivery by aliasing (e.g., by a DNS CNAME) given content provider domains or sub-domains to domains that are managed by the service provider's authoritative domain name service. End users that desire the content are directed to the distributed computer system to obtain that content more reliably and efficiently. Although not shown in detail, the distributed computer system may also include other infrastructure, such as a distributed data collection system 108 that collects usage and other data from the edge servers, aggregates that data across a region or set of regions, and passes that data to other back-end systems 110, 112, 114 and 116 to facilitate monitoring, logging, alerts, billing, management and other operational and administrative functions. Distributed network agents 118 monitor the network as well as the server loads and provide network, traffic and load data to a DNS query handling mechanism 115, which is authoritative for content domains being managed by the CDN. A distributed data transport mechanism 120 (comprising a metadata control server and a set of staging servers) may be used to distribute control information (e.g., metadata to manage content, to facilitate load balancing, and the like) to the edge servers.

Figure 2:
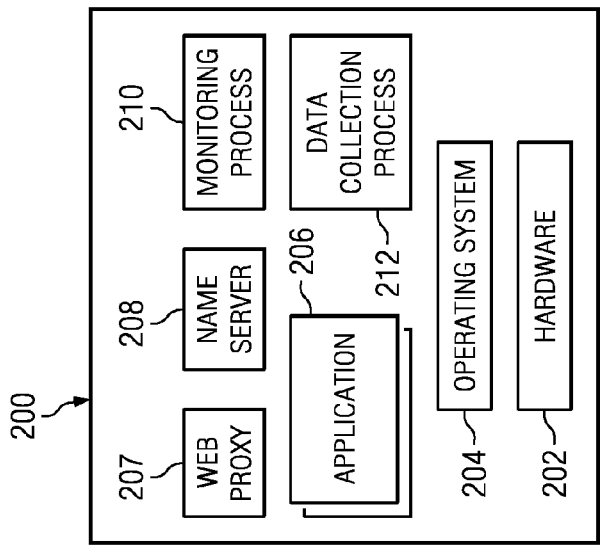
FIG. 2 is a simplified block diagram of a representative CDN edge machine on which the disclosed techniques may be implemented.

As illustrated in FIG. 2, a given machine 200 comprises commodity hardware (e.g., an Intel Pentium processor) 202 running an operating system kernel (such as Linux or variant) 204 that supports one or more applications 206a-n. To facilitate content delivery services, for example, given machines typically run a set of applications, such as an HTTP proxy 207 (sometimes referred to as a "global host" or "ghost" process), a name server 208, a local monitoring process 210, a distributed data collection process 212, and the like. The For streaming media, the machine typically includes one or more media servers, such as a Windows Media Server (WMS) or Flash server, as required by the supported media formats.

A CDN edge server is configured to provide one or more extended content delivery features, preferably on a domain-specific, customer-specific basis, preferably using configuration files that are distributed to the edge servers using a configuration system. A given configuration file preferably is XML-based and includes a set of content handling rules and directives that facilitate one or more advanced content handling features. The configuration file may be delivered to the CDN edge server via the data transport mechanism. U.S. Pat. No. 7,111,057 illustrates a useful infrastructure for delivering and managing edge server content control information, and this and other edge server control information can be provisioned by the CDN service provider itself, or (via an extranet or the like) the content provider customer who operates the origin server. U.S. Pat. No. 7,240,100 describes techniques for applying the edge server content control information at the edge server. The CDN may include a storage subsystem, such as described in U.S. Pat. No. 7,472,178. The CDN also may operate a server cache hierarchy to provide intermediate caching of customer content; one such cache hierarchy subsystem is described in U.S. Pat. No. 7,376,716. These disclosures are incorporated herein by reference.

The CDN may provide secure content delivery such as described in U.S. Publication No. 20040093419, or as described in U.S. Pat. No. 7,363,361. Secure content delivery as described therein enforces SSL-based links between the client and edge server process, on the one hand, and between the edge server process and an origin server process, on the other hand. This enables an SSL-protected web page and/or components thereof to be delivered (to the end user client browser) via the edge server. Typically, an SSL-protected web page is served to an end user process when an end user navigates to a web site merchant checkout page from an e-commerce web site that is being delivered via the CDN). The merchant checkout page typically is delivered from the origin server (not the CDN) and, in particular, from an application server (within the origin infrastructure) that comprises part of an order management system or gateway. In the past, the CDN service provider has not been involved in the processing of the actual order, in large part due to the sensitivity of handling credit card data during the payment transaction itself. As noted above, this techniques disclosed herein enable the CDN service provider to facilitate the payment transaction.

As used herein, the term "sensitive data" should be broadly construed, depending on the context. Thus, for example, in connection with an e-commerce transaction, which is the preferred embodiment, the term typically refers to any PCI sensitive data, such as credit or debit card number, bank account number, and the like. The "sensitive data" also may be identity information (such as personally identifiable information (PII)), health care information (such as HIPAA-related data), finance information (such as GLBA-related data), other confidential information, and the like.

Handling Sensitive Data

As noted above, the distributed and shared network infrastructure as described above is used, among other purposes, to deliver content from web sites, typically the web sites of CDN customers. Representative web sites include e-commerce retailers at which end users may shop and purchase products and services. In the prior art, CDN service providers provide the content delivery for these on-line retailers but, when it comes time for an end user to complete a purchase, the associated payment services are handled by third parties. This is the case even if the CDN provides secure content delivery, e.g., over SSL or TLS links, such as described in U.S. Publication No. 20040093419.

The disclosed subject matter extends the CDN infrastructure to facilitate payment services within that infrastructure. Because the providing of payment services involves the handling of end user credit card and other sensitive user data, there is a need to enhance the operation of the CDN to ensure that such data remains fully protected. A method of securing sensitive data (e.g., end user credit card information) is described below. In short, the technique allows the CDN service provider to process credit cards (and perhaps other personally identifiable information or "PII") without storing any data that could be exploited by a hacker to retrieve the actual card numbers (or other PII). Even if a hacker recovered everything that the CDN has stored, the hacker would not be able to reveal any confidential information.

The high level technique is now described. According to this disclosure, and in the context of protecting PCI data, a CDN key pair (PK_I, SK_I) is created for each card issuer I (e.g., VISA or AMEX). Thus, for issuer I, PK_I is the public key, and SK_I is the secret key. According to this disclosure, the value of SK_I is not stored on or in association with the CDN but, rather, only at the site of card issuer I (or some other location designated by the issuer but, once again, not on the CDN).

An end user visits the e-commerce web site in the usual manner. Typically, the CDN serves the non-secure pages of the site in the usual manner, such as described in U.S. Pat. No. 7,596,619. As the end user navigates through the site, he or she may identify certain products or services that he or she desires to purchase. One common technique that is used for this purpose is to associate a "shopping cart" (or, more generally, a data structure) with the user's browsing session. When the user selects an item for purpose, information about the item is stored in the cart. Then, when the user indicates a desire to "checkout" from the site (i.e., to purchase the items in the shopping cart), typically the CDN sets up a pair of SSL-links (although the shopping session may have initiated over SSL). In the usual case, a first secure link is established between the end user browser and the edge server, and a second link is established between the edge server and the origin server order management application.

After the SSL links are established, the origin server typically serves a "checkout" page. The end user then enters his or her credit card or other PII-related information, and hits "enter" on his or her browser. This creates an HTTP POST message, which includes the sensitive data. The sensitive data thus is received at the CDN edge server. According to the subject disclosure, however, instead of passing this data on through to the origin server, the edge server recognizes the POST, removes the PCI data, and computes a function. In particular, if the end user's credit card (CC) is from some issuer J, the CDN edge server process computes $V=PK\_J(CC)$ and then immediately discards the true credit card CC. In particular, the CC data is not stored on disk or other persistent store, and in-memory storage is kept to a minimum (just what is necessary to facilitate the above-described computation). According to this disclosure, all future processing of the card (and thus the CC) is done using V.

Preferably, the edge server maintains a database of tokens. The database may be in the form of an array, a linked list, an index table, or any other convenient data structure. A hash table may also be used. A token (or, more generally, a "data string") associates a value V with an identifier W associated with a web site (or portion thereof, including sub-domain). In response to receipt of the POST and the calculation of the value V, the edge server process then performs a lookup in the database to determine if the CDN has processed V for this web site W. If so, a token T for (V, W) will be present in the database. If (as a result of the lookup) it is determined that the CDN has processed V for this web site W before, the edge server sends the token T for (V, W) to the order management system to which the edge server is now coupled (on its forward processing side). If, however, it is determined that the CDN has not processed V for this site (because there is no such token in the database), the server randomly creates a new token T for (V, W). The new token is unique for W. The edge server process adds the new token to its database and then sends T to the web site over the forward connection.

The processing of tokens proceeds in the natural way until the web site order management system wants the CDN to process a request for authorization, or request for payment for a token T. The order management system communicates with the edge server process over the connection that is maintained (preferably in a persistent manner) between the two. When the edge server receives a response from the order management system indicating that the CDN edge server process should then "authorize" the transaction or make the actual payment request, the CDN edge server uses the token T and the value W to retrieve the value of V. The CDN edge server processor then opens up a new connection, to a card issuer network for J. Because the CDN edge server no longer maintains CC, however, it cannot transmit it; instead, the CDN edge server just sends V to the card issuer network. This value is sent via an intermediate (or subordinate) request, as the request typically is made while the overall checkout process is on-going. In a process external to the CDN, the card issuer J (or its delegate) then uses the secret key value SK_J to decrypt and retrieve CC.

For additional security, the decryption by or on behalf of card issuer J using SK_J preferably is done only if the transmission of V has been authenticated to have come from a CDN server.

A key advantage to this approach is security. Even if the CDN edge server is compromised, no credit card data is lost because the CDN edge server does not maintain such data. Moreover, because only the secret key SK_J can be used to retrieve the card numbers, access to the CDN edge server does not compromise the PCI data, because the secret key preferably resides only at the issuer (or on some server that the issuer has some degree of control over). (A CDN server may also be positioned at the card issuer). Thus, using this approach, a CDN service provider has no greater risk of exposure for payment services than it would if it were just passing the credit card to the CDN customer. Indeed, the risk is lower because the CDN provider no longer sends the card anywhere using the described above. While it is possible that the values of PK_J (CC) might be exposed by a hacker, these values are only of use if they are sent by the CDN. Thus, if PK_J (CC) is sent by another entity, then the card issuer would have knowledge, a priori, that the edge server has been compromised (and the value stolen) because it would have been encrypted using a CDN service provider key pair but not sent from a CDN machine.

Figure 3:
FIG. 3 is a block diagram of an edge server process interacting with a merchant origin server and an third party credit card issuer according to the teachings of this disclosure.

FIG. 3 illustrates a typical use case scenario. In this example, the client browser (or equivalent rendering engine) sends an HTTP POST (or equivalent) message to the edge server 300 during an order checkout to the merchant origin server 302. Origin server 302 has an associated order management system and database 304. The edge server 300 also interfaces to a card issuer payment gateway 306 that is associated with payment gateway database 308. The edge server comprises a token database, a public key PK associated with each issuer (such as the issuer associated with gateway 306), together with software (one or more computer programs, processes, utilities or the like) to carry out the above-described functionality. In particular, this software receives the HTTP POST, parses it to remove the sensitive data, generates the value V, retrieves (or creates the token T), and forwards the POST with the sensitive data replaced with the token. When the merchant origin server 302 requests transaction authorization or payment (e.g., by returning the token T), the CDN edge server performs this function by making the intermediate (subordinate) request to the payment gateway (which holds the secret key SK needed), passing the value V, and receiving the response (e.g., the payment authorization or the like). In this manner, the edge server performs or facilitates the payment service without exposing the sensitive data, which is deleted upon generation of the value.

The disclosed technique may have many variants. Thus, for example, instead of discarding the CC, the CDN edge server process may maintain some small portion thereof, such as the last four (4) digits, or some arbitrary CDN customer-defined data payload. As another alternative, the edge server process may first pad the CC with CDN-specific data before generating PK_J (CC). Optionally, the edge server process may extend this step to add other obfuscation data to prevent rainbow attacks against the token store. The functionality described herein may be used with or without credit card tokenization, which is a technique whereby a credit card number is exchanged with a token (by a third party token provider).

As another variant, the encryption step may be carried out on an end user device using CDN-provided client software, thereby ensuring that the credit card number is never even received with the edge server infrastructure.

The public key PK_J may be maintained secret for added security.

In another alternative approach, a second level of encryption using a secret CDN key is also used. In this approach, a public decryption key is then provided to the card issuer (or its delegate). This enables an extra level of authentication, namely, a way to verify that the transmission comes from the CDN and not some unauthorized intermediary. Other cryptographic techniques may be used as required. Thus, for example, the edge server may apply a digital signature to the value V.

The method described here covers the case where the protected information (e.g. a credit card number) only needs to be sent to a single entity (e.g., the network for the card issuer). The subject disclosure is not limited to this scenario. In the event the sensitive data (e.g., a medical record or the like) needs to be sent to multiple entities (e.g., various hospitals), then the edge server process creates and stores an encrypted copy of the data for each entity that requires it (using the secret key for each such entity). This requires that the CDN know ahead of time the identities of those entities. If this is not possible, the CDN service provider may retain a copy of a secret key in a highly secure location and manner so that it can recover the original version of the protected information (and, in particular, so that it could be encrypted later using an as-yet unknown public key).

The above-described technique may be used to secure any sensitive data within the context of a CDN service.

The above-described edge server process preferably is implemented in computer software as a set of program instructions executable in one or more processors, as a special-purpose machine. In one embodiment, the edge server process is an HTTP proxy that has been enhanced to provide the recited functions. Typically, an instance of the process is instantiated per HTTP request received from an end user browser, and that process instance maintains appropriate data structures to facilitate the processing described. The edge server process comprises a front end portion to which the client browser is coupled, and a back end portion to which the process is coupled to the origin server gateway (or the card issuer network, as described). The edge server process is capable of opening up and maintaining multiple connections. Control over the edge server process may be maintained using XML-based metadata provided to the edge server. Thus, because the edge server typically is handling content for multiple CDN customers, each CDN customer may provide its own unique configuration that is enforced at the edge server.

Representative machines on which the subject matter herein is provided may be Intel Pentium-based computers running a Linux or Linux-variant operating system and one or more applications to carry out the described functionality. One or more of the processes described above are implemented as computer programs, namely, as a set of computer instructions, for performing the functionality described.

Having described our invention, what we now claim is set forth below.

The invention claimed is:

1. A method to protect sensitive data, comprising:
   receiving a message that includes sensitive data, the message directed to a third party domain;
   determining an identity of an issuing entity associated with the sensitive data;
   parsing the message to extract at least a portion of the sensitive data;
   applying to the portion of the sensitive data extracted a public key of the issuing entity whose identity was determined to generate a value V;
   determining whether the value V is associated with an identifier W associated with the third party domain;
   in response to determining that the value V is associated with an identifier W associated with the third party domain, retrieving a token T that associates (V,W), and forwarding the message including the token onward to the third party domain;
   in response to determining that the value V is not associated with an identifier W associated with the third party domain, generating a new token that associates (V,W), and forwarding the message including the new token onward to the third party domain;
   receiving a response from the third party domain that includes one of: the token and the new token, previously forwarded with the message;
   in response to receiving the response from the third party domain, retrieving the value V and issuing a new request including the value V, the new request issued to a computing entity at which a secret key associated with the public key is available; and
   receiving a response from the computing entity indicating that a transaction associated with the sensitive data is authorized to proceed, the computing entity having applied the secret key to the value V to identify the sensitive data;
   wherein one or more operations of the method are carried out in software executing in a hardware processor.

2. The method as described in claim 1 wherein the sensitive data is PCI data.

3. The method as described in claim 2 wherein the PCI data is a credit card number.

4. The method as described in claim 1 wherein the operation of retrieving the value V and issuing a new request includes using the token or new token received from the third party domain together with the value W to retrieve the value V.

5. The method as described in claim 1 wherein the response from the third party domain is a payment request.

6. The method as described in claim 1 wherein the operation of applying to the sensitive data the public key of the issuing entity includes padding the sensitive data with given data before applying the public key.

7. The method as described in claim 6 wherein the given data is data associated with a content delivery network.

8. The method as described in claim 6 wherein the given data is obfuscation data to prevent a rainbow attack.

9. The method as described in claim 1 wherein the portion of the sensitive data extracted is all of the sensitive data in the message body.

10. The method as described in claim 1 wherein the portion of the sensitive data extracted is configurable.

* * * * *